US010920262B2

(12) United States Patent
Nanjo et al.

(10) Patent No.: US 10,920,262 B2
(45) Date of Patent: Feb. 16, 2021

(54) CELL MEASUREMENT METHOD

(71) Applicant: KURASHIKI BOSEKI KABUSHIKI KAISHA, Okayama (JP)

(72) Inventors: Yuko Nanjo, Osaka (JP); Hiroyuki Asano, Osaka (JP); Isao Miyagawa, Osaka (JP); Yoshio Takada, Osaka (JP)

(73) Assignee: KURASHIKI BOSEKI KABUSHIKI KAISHA, Okayama (JP)

( * ) Notice: Subject to any disclaimer, the term of this patent is extended or adjusted under 35 U.S.C. 154(b) by 45 days.

(21) Appl. No.: 16/345,728

(22) PCT Filed: Oct. 20, 2017

(86) PCT No.: PCT/JP2017/037954
§ 371 (c)(1),
(2) Date: Apr. 29, 2019

(87) PCT Pub. No.: WO2018/084002
PCT Pub. Date: May 11, 2018

(65) Prior Publication Data
US 2019/0256885 A1    Aug. 22, 2019

(30) Foreign Application Priority Data
Nov. 1, 2016    (JP) .............................. JP2016-213995

(51) Int. Cl.
*G01N 1/30*    (2006.01)
*C12Q 1/06*    (2006.01)
(Continued)

(52) U.S. Cl.
CPC .................. *C12Q 1/06* (2013.01); *G01N 1/30* (2013.01); *G01N 21/27* (2013.01); *G01N 33/48* (2013.01);
(Continued)

(58) Field of Classification Search
CPC combination set(s) only.
See application file for complete search history.

(56) References Cited

U.S. PATENT DOCUMENTS 5,356,793 A * 10/1994 Koezuka ............ G01N 15/1475
382/133
5,712,161 A * 1/1998 Koezuka .............. C12N 5/0012
435/177
(Continued)

FOREIGN PATENT DOCUMENTS

JP    H03285696    12/1991
JP    H10115612    5/1998
(Continued)

OTHER PUBLICATIONS

"International Search Report (Form PCT/ISA/210) of PCT/JP2017/037954," dated Jan. 23, 2018, with English translation thereof, pp. 1-4.

Primary Examiner — Tsung Yin Tsai
(74) Attorney, Agent, or Firm — JCIPRNET

(57) ABSTRACT

[Problem] To provide a highly accurate cell measurement method. [Solution] A cell measurement method comprising: a step of staining target cells with a dye; an image obtaining step for obtaining an image of the target cells; a discrimination step for discriminating the target cells from contaminating cells by applying multi-stage binarization processing to the image; a step of eliminating noises due to the contaminating cells from the image based on the result of the discrimination step; and a step of evaluating an amount of target cells by integrating an index value of cell amount in the image from which the contaminating cells have been eliminated.

20 Claims, 12 Drawing Sheets

(51) Int. Cl.
    *G01N 21/27*     (2006.01)
    *G01N 33/483*    (2006.01)
    *G06T 7/00*      (2017.01)
    *G01N 33/48*     (2006.01)

(52) U.S. Cl.
    CPC ....... *G01N 33/483* (2013.01); *G01N 33/4833* (2013.01); *G06T 7/00* (2013.01); *G06T 7/0012* (2013.01)

(56) References Cited

U.S. PATENT DOCUMENTS

| | | | | |
|---|---|---|---|---|
| 7,760,925 | B2* | 7/2010 | Sakurai | G06T 7/0012 |
| | | | | 382/129 |
| 8,765,464 | B2* | 7/2014 | Minamigawa | C12N 5/0018 |
| | | | | 435/325 |
| 2009/0055147 | A1* | 2/2009 | Miyake | G01N 33/5005 |
| | | | | 703/11 |
| 2016/0289662 | A1* | 10/2016 | Miyagawa | C12Y 304/21004 |
| 2018/0038796 | A1* | 2/2018 | Ichitani | G01N 21/6458 |
| 2018/0252636 | A1* | 9/2018 | Nanjo | C12M 1/3476 |

FOREIGN PATENT DOCUMENTS

| | | |
|---|---|---|
| JP | 2002312761 | 10/2002 |
| JP | 3363445 | 1/2003 |
| JP | 2008011797 | 1/2008 |
| JP | 2014063019 | 4/2014 |
| WO | 9518216 | 7/1995 |
| WO | 2016152159 | 9/2016 |
| WO | 2017033809 | 3/2017 |

\* cited by examiner

| | G0 Luminosity image | G1 Binarization level 1 | G2 Binarization level 2 | G3 Binarization level 3 |
|---|---|---|---|---|
| C | Cancer cells | Round | Round | |
| FF | Fibroblasts / Overlapping portion | Not round | Round | |
| CF | Fibroblasts / Cancer cells | Not round | Round | Round |

Figure 9

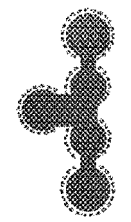
Figure 11
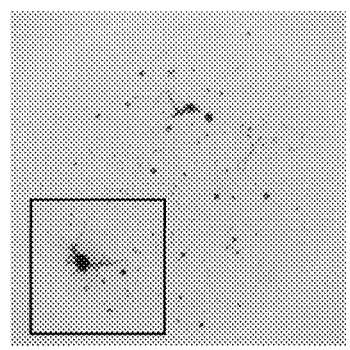 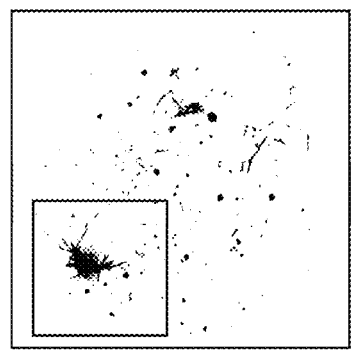
Figure 12A  Figure 12B

CELL MEASUREMENT METHOD

CROSS-REFERENCE TO RELATED APPLICATION

This application is a 371 application of International PCT application serial no. PCT/JP2017/037954, filed on Oct. 20, 2017, which claims the priority benefit of Japan application no. 2016-213995, filed on Nov. 1, 2016. The entirety of each of the abovementioned patent applications is hereby incorporated by reference herein and made a part of this specification.

TECHNICAL FIELD

The present invention relates to a method for measuring a cell amount.

BACKGROUND ART

In a susceptibility test for an anticancer agent against epithelial malignant tumor, sarcoma, etc., a cancer cell brought into contact with an anticancer agent and a cancer cell not brought into contact with the anticancer agent are cultured under the same condition, and the proliferation degrees of the cancer cells after cultivation are compared so as to evaluate susceptibilities of the cancer cells to the anticancer agent. As the proliferation of the cancer cell is less, the anticancer agent with high anticancer effect is expected.

As a method for culturing cancer cells, Patent Documents 1 to 5 describe methods for culturing cancer cells by embedding them in a collagen gel. This collagen gel embedding cultivation is known to proliferate cancer cells better compared to a surface cultivation in which cancer cells are cultured on a surface of agar or the like.

As a method for quantitating a cultured cancer cell, Patent Document 1 describes a method in which a proliferated cancer cell is imaged with a TV camera or the like, and then obtained image information is electronically image-analyzed to calculate estimated volume values of cancer cell colonies. In addition, Patent Document 3 describes a method in which a cancer cell cultured in a collagen gel is stained with a dye, imaged, and quantitated on the basis of the shade of an image.

PRIOR ART DOCUMENTS

Patent Documents

Patent Document 1: JP H03-285696 A
Patent Document 2: WO 95/18216
Patent Document 3: JP H10-115612 A
Patent Document 4: JP Pat. No. 3363445
Patent Document 5: JP 2008-11797 A

SUMMARY OF INVENTION

Problem to be Solved

The cancer cell quantitating methods described in Patent Document 1 and Patent Document 3 had problems of further improvement for quantitative precision. The susceptibility tests to anticancer agents have been conventionally performed using surgical materials taken from cancer patients as starting materials. On the other hand, there has been growing demand for an anticancer agent susceptibility test using a biopsy material as a starting material, in which cells are sampled with a puncture needle or the like for progressive recurring cases not indicated of operation for which any surgical material is unavailable or preoperative chemotherapy which has increased in recent years. However, for the biopsy material, since tissue pieces that can be sampled are smaller than surgical materials, it is required in the anticancer agent susceptibility test to precisely quantitate less than one-tenth cell amount of that in the conventional test. It was difficult by the method described in Patent Document 1 or Patent Document 3 to precisely quantitate such a small amount of cancer cell.

In addition, one of the causes of impairing precision of quantification was confusion of cancer cells and fibroblasts as the fibroblasts are stained with a dye together with the cancer cells. Patent Document 1 describes that image analysis discriminates between cancer cells and fibroblasts by their shapes and shade of images. Patent Document 3 describes that cancer cells are distinguished from fibroblasts by the shade of the image utilizing the fact that fibroblasts tend to be stained much less than cancer cells. However, they could not be precisely discriminated in some cases where they were densely mixed, even by using these methods.

The present invention has been made in view of the above, and an object of the present invention is to provide a cell measurement method with higher quantitative precision.

Solution to Problem

The cell measurement method of the present invention comprises: a step of staining target cells with a dye; an image obtaining step for obtaining an image of the target cells; a discrimination step for discriminating the target cells from contaminating cells by applying multi-stage binarization processing to the image; a step of eliminating noises due to the contaminating cells from the image based on the result of the discrimination step; and a step of evaluating an amount of target cells by integrating an index value of cell amount in the image from which the contaminating cells have been eliminated.

Here, the target cells means cells to be measured. In addition, the multi-stage binarization processing means performing multiple binarization processings while varying threshold values. In addition, noises means unnecessary image information not derived from the stained target cells. Furthermore, the index value of cell amount means an index which increases or decreases depending on the amount of the cell, such as a gray value of the image or an absorbance calculated from the gray value of the image. This method eliminates the influence of the noises due to contamination cells resulting in errors, so that the cell amount can be precisely measured.

Preferably, when an island-like section is substantially circular in two binarization processings by using two threshold values which are different by a predetermined reference difference or more, and thus it can be estimated that the island-like section is substantially circular between these two threshold values regardless of the magnitude of the threshold values, the discrimination step comprises a step of judging that the island-like section is substantially spherical cells.

More preferably, when a percentage of arcs with respect to a contour of an island-like section is greater than or equal to a predetermined value in two binarization processings by using two threshold values which are different by a predetermined reference difference or more, and thus it can be estimated that the percentage of the arcs with respect to the contour of the island-like section is greater than or equal to the predetermined value between the two threshold values regardless of the magnitude of the threshold values, the discrimination step comprises a step of judging that the island-like section is an aggregate of substantially spherical cells.

Preferably, in the discrimination step, the binarization processings are performed while sequentially increasing or decreasing the threshold values.

Preferably, the target cells are cancer cells and the contaminating cells are fibroblasts.

Preferably, the target cells are cells cultured by being embedded in a collagen gel.

The image may be a luminosity image of a transmission image obtained by imaging the target cells. In this case, the threshold value is a luminosity value. Alternatively, the image may preferably be an absorbance image based on a transmission image obtained by imaging the target cells. Here, the absorbance image means an image obtained by converting the luminosity value of each pixel of the luminosity image to the absorbance and quantizing it. In this case, the threshold value is a quantized absorbance.

Preferably, the index value of cell amount is an absorbance, and the evaluating the amount of target cells is performed by calculating an estimated volume value of the target cells.

Preferably, the image obtaining step consists of: a step of obtaining a first image and a second image which are transmission images for a first light and a second light to which the dye has different absorbance; and a step of obtaining a first noise-eliminated image by dividing each of the first image and the second image into a plurality of divided regions and comparing the first image and the second image for each of the divided regions so as to eliminate noises. Here, the divided region of the image means a region composed of one or more pixels on the image.

Preferably, the first image and the second image are obtained on the basis of the transmission image taken with one color camera while concurrently applying the first light and the second light.

Alternatively, preferably, the first image and the second image are obtained on the basis of the transmission image obtained by independently taking each image using one camera while sequentially applying the first light and the second light.

Effects of Invention

According to the cell measurement method of the present invention, the cell amount can be precisely evaluated even when the amount of target cells is relatively small with respect to noise components such as contaminating cells or dusts. In particular, the target cells and the contaminating cells can be precisely discriminated even when they are densely mixed, and thus the target cell amount can be precisely evaluated.

BRIEF DESCRIPTION OF DRAWINGS

FIG. 9 is a diagram for explaining a multi-stage binarization processing of cells overlapping each other.

FIG. 11 is a diagram for explaining the multi-stage binarization processing of the island-like section which is an aggregate of spherical cells.

FIGS. 12A and 12B shows an original image (FIG. 12A) and a binarized image (FIG. 12B) of an absorbance image of Example.

DETAILED DESCRIPTION OF EMBODIMENTS

Figure 1:
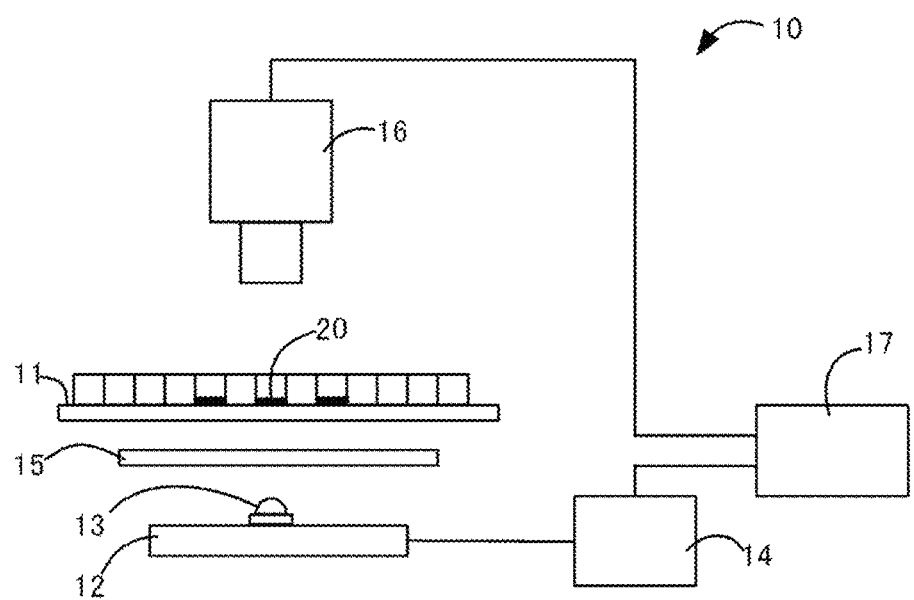
FIG. 1 shows a configuration example of a cell measuring apparatus used in the first embodiment of the present invention.

First, a method for discriminating between target cells and contaminating cells by a multi-stage binarization processing is described with reference to FIGS. 8 to 11. Here, the description is made based on an assumption that spherical cancer cells are target cells and spindle-shaped fibroblasts are contaminating cells in a luminosity image (gray scale image) of the stained cells.

Whether an island-like section (hereinafter referred to also merely as "island") separated from others on the image has a "round" shape, i.e., a substantially circular shape can be judged by several methods. For example, with reference to FIG. 8, it can be judged by whether or not a vertical/horizontal ratio of the island is close to 1 (P of FIG. 8), whether or not an aspect ratio of the island is close to 1 (Q of FIG. 8), whether or not a ratio of the area of the island to the area of a circumscribed rectangle (R of FIG. 8), or whether or not a ratio of the square of a periphery length to the area is close to 4π (S of FIG. 8). It is preferable to judge whether or not the island is round by using a plurality of methods among these methods in combination. This is for lowering the probability of erroneous recognition of a non-round island as a round island. For example, it is difficult to discriminate between a round island and a star-shaped island by the methods in P and Q of FIG. 8, and it is difficult to discriminate between a round island and a spindle-shaped island by the methods in R and S of FIG. 8.

Next, with reference to FIG. 9, the case where the cells overlap each other is considered. The first row (C) shows an island composed of an isolated cancer cells, the second row (FF) shows an island in which spindle-shaped fibroblasts cross each other, and the third row (CF) shows an island in which cancer cells and a fibroblast overlap. A column G0 shows luminosity images of these islands (hereinafter the image in the column G0 is referred to as an "image G0"; the same applies to the others).

The threshold value is set to a high luminosity (light color) level (binary level 1) to binarize the images G0 (column G1). For these images G1, when a judgement is made by the above-mentioned methods on whether or not the islands after the binarization processing are round, the island C is judged to be round, the island FF is judged to be non-round, and thus the cancer cell is correctly discriminated from the fibroblast. However, the island CF is judged to be non-round, and the cancer cell which overlaps the fibroblast will be overlooked.

The threshold value is set to a lower luminosity (darker color) level (binary level 2) to binarize the images G0 (column G2). For these images G2, a judgement is made on whether or not the islands are round. The island C is judged to be round, i.e., the conclusion does not change. The island CF is judged to be round, and the cancer cell is correctly discriminated. However, this time, the island FF is also judged to be round, and the crossing portion of the fibroblasts is erroneously recognized as the cancer cell.

The threshold value is set to a further lower luminosity (further darker color) level (binary level 3) to binarize the images G0 (column G3). For these images G3, a judgment is made on whether or not the islands are round. The island C and the island FF are disappeared. The island CF is judged to be round, and the cancer cell is correctly discriminated.

In this way, when a judgment is made on whether or not the island is round on the basis of only one binarized image, there is a risk of erroneous recognition between the cancer cell and the fibroblast. However, it is possible to discriminate between the cancer cell and the fibroblast for any of the island C, the island FF, and the island CF, by sequentially performing the binarization processings (G1 to G3) while varying the threshold value in a stepwise manner, and judging that the island is the cancer cells when the island is round in consecutive two or more binarization processings.

Figure 10:
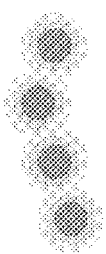
FIG. 10 is a diagram for explaining the multi-stage binarization processing of the island-like section which is an aggregate of spherical cells.

With reference to FIG. 10, it is possible to discriminate the cancer cells from fibroblasts from the above-mentioned method even when cancer cells are crowded to some degree.

Furthermore, in the multi-stage binarization processing, it is preferable to judge whether or not the island is an aggregate of cancer cells by a percentage of arcs with respect to a contour of each of the islands, in addition to the judgement on whether or not each of the islands after the binarization processing is round. With reference to FIG. 11, when the cancer cells are more crowded compared to FIG. 10, the cancer cells do not separate even if the threshold value is varied, and thus the island may not be judged to be round. Here, in the image G1 and the image G2 in FIG. 11, a portion of the contour of the island indicated by a dashed line on its outside is formed of an arc. Thus, when the percentage of the arcs with respect to the contour of the island is greater than or equal to a predetermined threshold value in consecutive two or more binarization processings, it can be judged that the island is an aggregate of cancer cells.

Known methods can be used for extracting the contour, and for determining the percentage of the arcs with respect to the contour. For example, a method described in Katsuhiko Sakagami and Mikio Takagi, "Separation of particle images overlapping each other by iterative operation", Journal of Information Processing Society of Japan, September 1983, Vol. 24, No. 5, pp. 561-567, can be used. A portion in the contour which can be approximated by a circle is judged as an arc, and the percentage of the contour length of the portion which is judged as an arc with respect to the contour length of the entire island is calculated.

Since if the predetermined value (hereinafter referred to as "reference percentage") which becomes judgement criteria of whether or not the island is an aggregate of cancer cells is set too low, the probability of erroneous recognition of anything that is not the aggregate of cancer cells as the aggregate of cancer cells increases. Therefore, the reference percentage is set to preferably 40% or more, more preferably 50% or more. On the other hand, if the reference percentage is set too high, the probability of erroneous recognition of the aggregate of cancer cells as the others increases. Therefore, the reference percentage is set to preferably 80% or less, more preferably 70% or less.

As a first embodiment of the cell measurement method of the present invention, a method of quantitating cancer cells in an anticancer agent susceptibility test will be described below.

Prior to the cultivation, tissues sampled from a living body are subjected to dispersion treatment such as chopping and digestion of intercellular substances by a cell dispersion enzyme treatment. In some cases, separation treatment is subsequently carried out in which unnecessary cells such as blood corpuscles are removed by preliminary cultivation and living cells are collected.

Various known methods can be used to prepare a cultured sample. Above all, a three-dimensional cultivation is preferably used. More preferably, a collagen gel embedding cultivation is used. This method allows preferable cultivation and subsequent quantitation of the cancer cell even when the amount of cancer cells used for cultivation is small.

The procedure according to the collagen gel embedding cultivation is as follows. A separated and dispersed cell is blended into a collagen solution. At this time, besides collagen, various components necessary for cultivation can be added to the collagen solution. For example, a buffer which is the same as or similar to the physiological condition of the target cell can be added to the collagen solution. The collagen solution containing the cancer cell is dropped onto the supporting surface in the culture container to form a collagen gel in a form of droplet, and the liquid medium is added into the culture container. Similarly, several samples are prepared. For some samples, an anticancer agent is added to the culture container, and after a predetermined time, the anticancer agent is washed away, and cultivation is carried out again.

After completion of the cultivation, a dye is added to the culture container to stain the cancer cell as a target cell. As a staining method, a staining method in conventional cancer cell cultivation can be applied. Specific examples include a Giemsa solution dyeing method, a crystal violet dyeing method, a neutral red (NR) dyeing method, a fluorescein diacetate (FDA) dyeing method, and dyeing methods using other fluorescent reagents. As a staining method, a method in which cancer cells can be selectively stained and components other than cancer cells are stained as little as possible, is preferable. Use of a living cell-staining method for selectively staining a living cell is suitable for measuring susceptibility to an anticancer agent, or the like. The NR staining method is preferable as a method capable of selectively staining only living cells among cancer cells.

After completion of staining, the dye is fixed within the cell with formalin and dried. In the dried collagen gel, moisture is released from the droplet-like collagen gel, so that the gel is in a form of flat face.

Next, a method for imaging a sample including a target cell and processing the image will be described with reference to FIGS. 1 to 5. A flowchart of the process is shown in FIG. 2.

Figure 2:
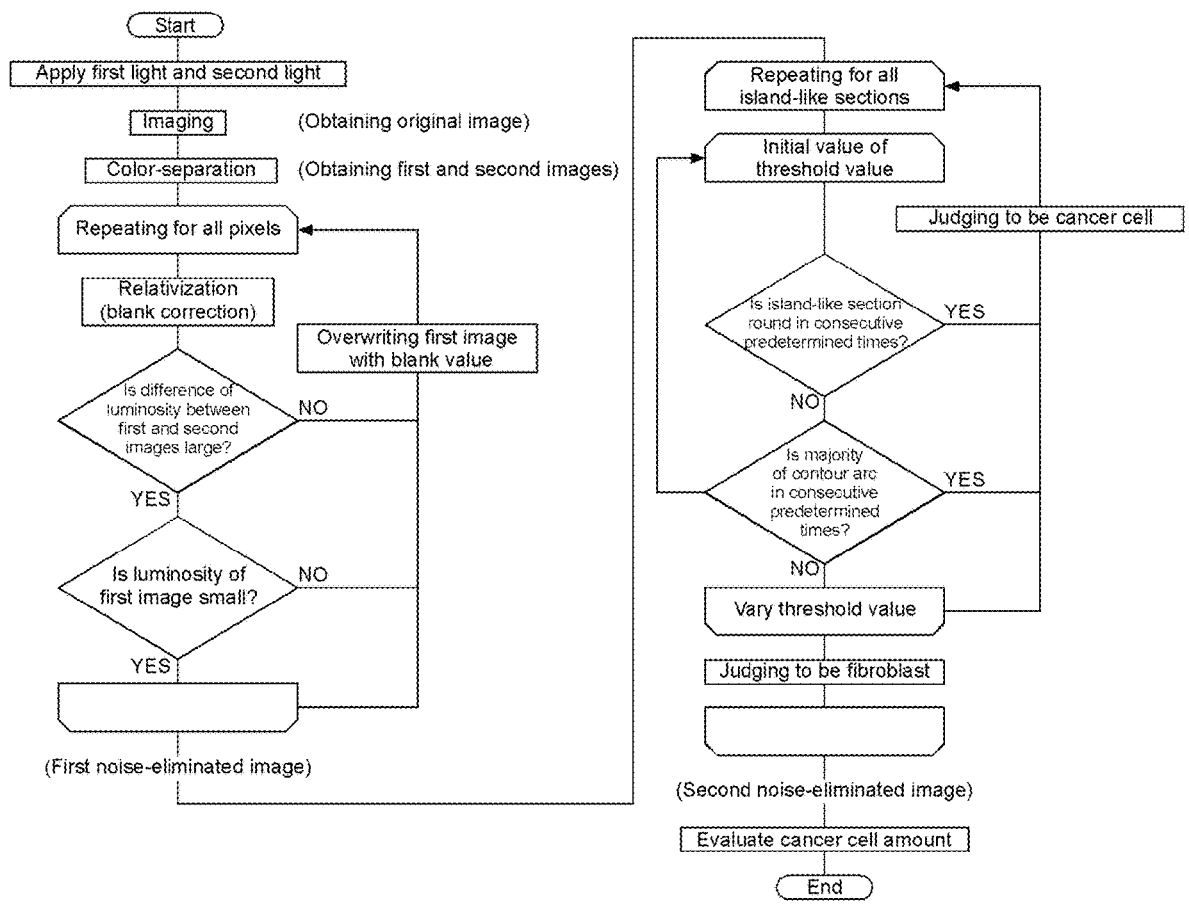
FIG. 2 is a flow chart of a cancer cell quantitating method according to the first embodiment of the present invention.

In FIG. 1, a measuring apparatus 10 according to the present embodiment comprises: a sample stage 11 on which a sample 20 is placed; an illumination 12 for illuminating the sample from below; a color camera 16 for imaging a transmission image of the sample; and an image processor 17. The illumination 12 comprises one LED package 13 and is connected to the illumination power supply 14. A light diffusion plate 15 is inserted between the illumination and the sample stage. In each LED package, an LED chip for emitting a first light (not shown) and an LED chip for emitting a second light (not shown) are incorporated.

Between the first light and the second light, there is a difference in absorbance by the dye which has stained the sample. In the present embodiment, the first light and the second light are concurrently applied to the sample, and the sample is imaged by one color camera to obtain one original image. This original image is color-separated, so that the first image as a transmission image for the first light and the second image as a transmission image for the second light can be obtained.

For the first light and the second light, it is preferable that the difference in absorbance by the dye therebetween is greater. In order to obtain sufficient measurement precision, a ratio of transmission loss between the first light and the second light in transmitting through the sample is preferably 1:1.5 or more, more preferably 1:2 or more. For that purpose, the difference in absorbance therebetween is preferably log 1.5≈0.18 or more, more preferably log 2≈0.30 or more. Since the absorbance varies depending on the measurement conditions, it is preferable to select wavelengths of the first light and the second light such that such a difference can be obtained under actual measurement conditions.

Figure 5:
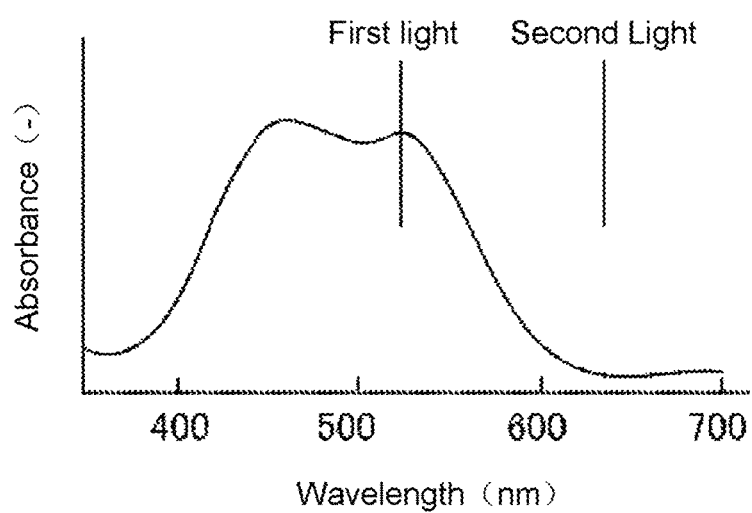
FIG. 5 shows an absorption spectrum of a neutral red.

For example, FIG. 5 shows absorption spectrum of neutral red (NR) at pH=7.1 (made from: Rika Obata et al., "Neutralization titration, and visible absorption spectrum of acid-base indicator", The Hiyoshi review of Natural Science, Keio University, No. 50, pp. 77-102, September 2011). The NR has an absorption band in a range of about 380 nm to 600 nm at this pH, and has an absorption peak at 462 nm and 518 nm. In this case, green light whose wavelength distribution overlaps with this absorption band can be selected for the first light, and red light whose wavelength distribution does not overlap with this absorption band can be selected for the second light.

As a light source for illumination, an LED is preferably used. This is because the wavelength distribution of LED is narrow and a difference between the first image and the second image is easy to clearly appear. Note that the physical form of illumination is not particularly limited. For example, the number of LED packages is not particularly limited. In addition, for example, an LED chip emitting the first light and an LED chip emitting the second light may be incorporated in one LED package as in the present embodiment, or an LED package emitting the first light and an LED package emitting the second light may be arranged alternately.

An image is constituted as an aggregate of many pixel data. Each pixel includes information representing a luminosity corresponding to a light intensity captured by image sensor elements of the camera. For example, if a gradation for inputting images is 8-bit gradation, the luminosity is represented by 256 different values from 0 to 255. If light is absorbed when transmitting through the sample, the relevant portion is dark on the transmission image, that is, the luminosity is low.

In the first image which is a transmission image for the first light, absorption by the NR is large, and thus if there are cancer cells stained with the NR in the cultured sample, the intensity of the transmitted light on the relevant portion is low. In addition, the larger the thickness of the cancer cell is, the lower the intensity of the transmitted light is, and the lower the luminosity of the image is. On the other hand, the second image which is a transmission image for the second light does not significantly reflect the presence amount of the cancer cells.

Herein, each of the first image and the second image is divided into a plurality of divided regions by the same method. The division by the same method means that a divided region of the first image and a corresponding divided region of the second image are the same in size, and imaged on the same place of the sample. In the present embodiment, one pixel is defined as one divided region. Since the first image and the second image are obtained from one original image, each pixel is a region obtained by dividing both images by the same method.

Figure 3:
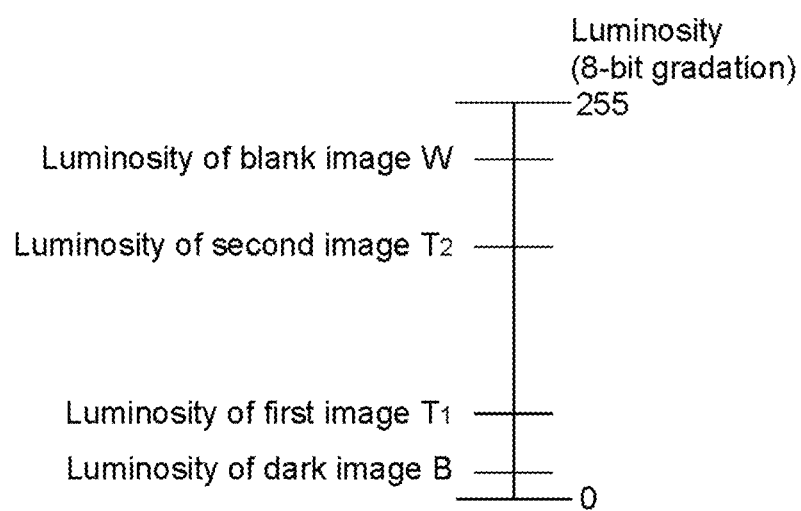
FIG. 3 is a diagram for explaining the luminosity of the image.

First, a blank image luminosity W obtained from image information of a sample containing no cancer cell is defined as an upper limit, and a dark image luminosity B obtained from image information in a dark state is defined as a lower limit, and relative values of the luminosity with respect to the upper and lower limit values are determined for each pixel to correct the first image and the second image. A blank image is an image in the brightest state obtained by imaging a blank sample treated through the same process as for the cultured sample of the cancer cell except that the cancer cell is not added. However, the blank image is not a complete white image because of the presence of a collagen gel matrix and the like. A dark image is an image in the darkest state in which light is prevented from entering by closure of a shutter of an imaging lens or the like. As shown in FIG. 3, the luminosity $T_1$ of the first image and the luminosity $T_2$ of the second image are between the luminosity W of the blank image and the luminosity B of the dark image.

Next, influence of noises is eliminated by comparing the first image and the second image.

Respective pixels are compared between the first image and the second image. If the difference or the ratio of the luminosities is less than a predetermined threshold value, the region of the relevant pixel is judged to have no cancer cell, and the pixel is excluded. More specifically, the data of the pixel is excluded from the data which is the basis for evaluating the cancer cell amount later. Specifically, for example, the first image may be corrected by overwriting the luminosity of the pixel with the luminosity of the blank image. Thereby, the luminosity of the pixel does not affect the evaluation of the cancer cell amount and that pixel is substantially excluded.

When the difference in luminosity is defined as a reference for the threshold value, for example the threshold value can be set to one eighth of the gradation number of luminosity. That is, in a case that the luminosity is represented by 8 bits/256 gradations, when the difference in luminosity between the first image and the second image is smaller than 32, the relevant pixel may be excluded. Alternatively, in a case that the ratio of the luminosity is defined as a reference, when the ratio in luminosity between the first image and the second image is lower than a predetermined threshold value, the relevant pixel may be excluded. More preferably, these threshold values are previously determined by a preliminary experiment.

Since opaque dusts do not transmit light regardless of the wavelength, it looks dark in both the first image and the second image. In addition, since bubbles contained in the dried collagen gel look dark on the image due to light refraction, the bubbles also look dark similarly in both the first image and the second image regardless of the wavelength of the light source. Consequently, these noises can be eliminated by excluding regions where there is no difference in luminosity between the first image and the second image.

Note that bubbles are particularly problematic when the cell amount is small in collagen gel embedding cultivation. If the cell amount is small, bubbles may remain in the dried collagen gel. Although the reason is unclear, it is considered that when the cell amount is large, gas in the gel passes through the interface between the cell and the matrix in the gel droplet mass to exit outside, whereas when the cell amount is small, gas in the gel does not thoroughly exit but remains.

Figure 4:
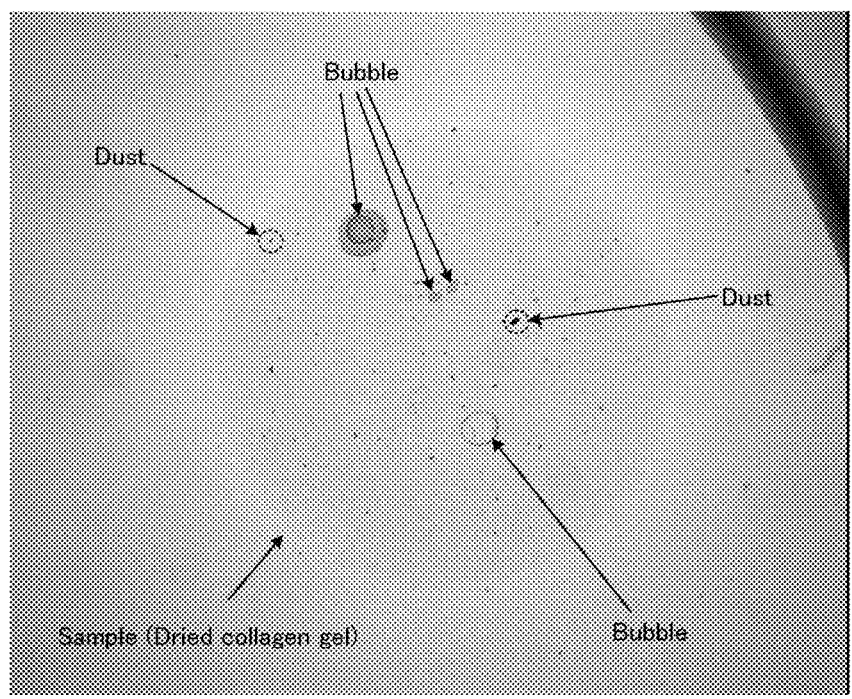
FIG. 4 is a picture for explaining an original image obtained by the cancer cell quantitating method according to the first embodiment of the present invention.

FIG. 4 shows a transmission image (original image) of a sample stained with NR. The first light was green light with a dominant wavelength of 528 nm and the second light was red light with a dominant wavelength of 625 nm. Note that FIG. 4 is a picture obtained by converting the original color image into a monochrome image, in which the resolution is also converted. The circular area at the center is the sample (dried collagen gel). Many fine dark spots scattered on the sample are cancer cells or colonies thereof, which are red in the original image, dark in the first image, and do not appear in the second image. Note that the dark spots surrounded by the dotted line are dusts, which are gray in the original image, and dark in the first image and the second image. The upper hatched ellipse and the lower hollow ellipse indicate noises due to bubbles, which are gray in the original image and dark in the first image and the second image.

Another cause of noise is contamination by fibroblasts. The fibroblast is stained with a dye such as NR together with the cancer cell, but the fibroblast is much more difficult to stain than the cancer cell, and its luminosity in the image is obviously higher than that of the cancer cell. Thus, when the luminosity of a pixel exceeds a predetermined threshold value in the first image, the region of the relevant pixel is judged to have the fibroblast, and the pixel is excluded. Specifically, for example, the first image may be corrected by overwriting the relevant pixel with the luminosity of the blank image. The threshold value can be determined by a preliminary experiment. Consequently, the noise arising from fibroblasts can be eliminated for the area where fibroblasts exist separated from cancer cells or the other fibroblasts.

The above processing is repeated for each of the divided regions over the entire area of the sample, so that the influence of the noises not resulting from light absorption by the cancer cell can be eliminated. The noise which can be eliminated by comparison of the first image and the second image in this way is referred to as "first noise". The first noise-eliminated image is obtained in this way.

Next, a multi-stage binarization processing is applied to the first noise-eliminated image.

In the multi-stage binarization processing, a plurality of binarization processings are performed while varying a threshold value to judge whether an island is round, and whether a percentage of arcs with respect to a contour of the island is greater than a predetermined value (reference percentage). Hereinafter, the case where the island is round and the case where the percentage of arcs with respect to the contour of the island is greater than the predetermined value are collectively referred to as "the island has a circular shape or the like".

An interval of varying the threshold value (hereinafter referred to as "threshold value interval") in the multi-stage binarization processing and a number of times of the binarization processings in which an island is judged to have a circular shape or the like required for the judgement that the island is cancer cells (hereinafter referred to as "reference number of times") are linked with each other. For example, the binarization processing is performed while increasing the threshold value stepwise, if the threshold value interval is small the reference number of times needs to be set high, and if the threshold value interval is large, the reference number of times may be set low. The threshold value interval and the reference number of time can be determined as follows.

Figure 15:
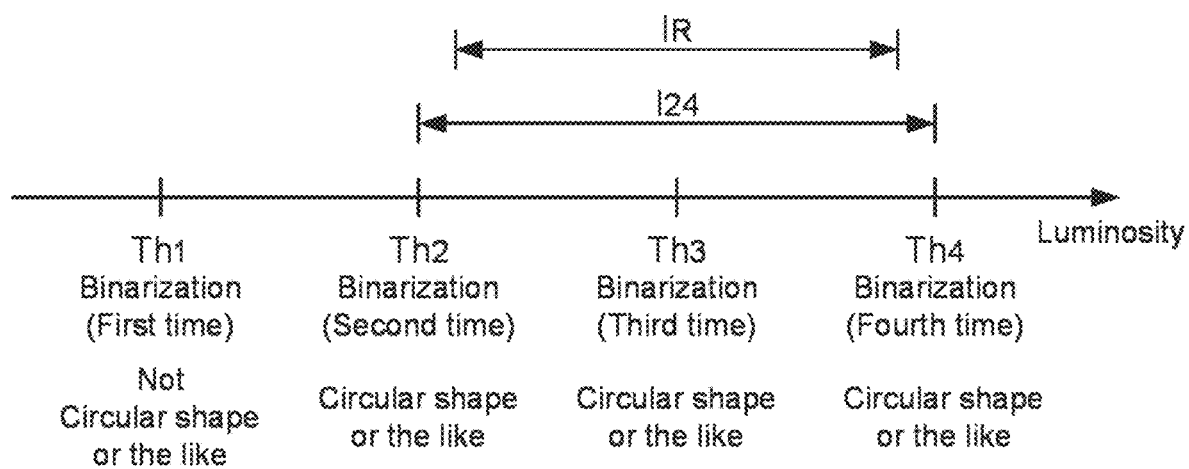
FIG. 15 is a diagram for explaining a reference section length or a reference difference in the multi-stage binarization processing.

In FIG. 15, the horizontal axis indicates luminosity, and each point on the horizontal axis indicates the judgement result after the binarization processing using the luminosity as a threshold value. It is assumed that the binarization processing was performed while increasing the threshold value stepwise, the island did not have a circular shape or the like in the first binarization processing (in which the threshold value was $Th_1$), and the island had a circular shape or the like in the second to fourth binarization processings (in which the threshold values were $Th_2$, $Th_3$, $Th_4$). Here, when a section between $Th_2$ and $Th_4$ on the luminosity line was defined as a section $I_{24}$, the island had a circular shape or the like in the binarization processings using a lower limit value $Th_2$ and an upper limit value $Th_4$ as the threshold values. Therefore, when performing the binarization using the luminosity included in the section $I_{24}$, it can be estimated that the island has a circular shape or the like regardless of the magnitude of the threshold values.

Then, in the case where the island after binarization processing has a circular shape or the like even if the threshold value is varied within a section of a certain predetermined length, the island is judged to be cancer cells. The predetermined length is referred to as a "reference section length", or a "reference difference" as a meaning of difference between a lower limit value and an upper limit value of the section. The reference section length and the reference difference are identical. Then, if the island has a circular shape or the like in both binarization processings using two threshold values different from each other by the reference difference or more, it can be estimated that the island has a circular shape or the like regardless of the magnitude of the threshold value between these two threshold values, and it can be judged that the island is composed of cancer cells.

In FIG. 15, when the difference between the threshold values $Th_2$ and $Th_4$ is greater than the reference difference $I_R$, it can be estimated that the island has a circular shape or the like after the binarization processings regardless of the magnitude of the threshold values by the fact that the island has a circular shape or the like in two binarization processings with two threshold vales $Th_2$, $Th_4$ different from each other by the reference difference $I_R$ or more. Therefore, since it can be estimated that the island has a circular shape or the like after the binarization processings even if the threshold values are varied within the section of the reference section length IR included between $Th_2$ and $Th_4$, it can be judged that the island is cancer cells.

The threshold value interval and the reference number of time of the binarization processing can be defined on the basis of this reference section length. For example, it can be set that: the threshold value interval: $\Delta \text{Th} = I_R$ and the reference number of time: twice; the threshold value interval: $\Delta \text{Th} = I_R/2$ and the reference number of time: three times.

When the luminosity is expressed by 256 gradations, the reference section length is set to preferably 70 or less, more preferably 40 or less. This is because if the reference section length is too large, the probability of overlooking of cancer cells increases. On the other hand, the reference section length is set to preferably 5 or more, more preferably 10 or more. This is because if the reference section length is too small, the probability of erroneous recognition of cells which are not cancer cells as cancer cells increases. For example, the probability of erroneous recognition of the overlapping portion of the fibroblasts shown in the second row (FF) in FIG. 9 as the cancer cell increases. If the number of gradations of luminosity is not 256, a preferable value of the reference section length according to the number of gradations can be determined using the same proportion to the number of gradations. In addition, further preferably, the reference section length is determined by a preliminary experiment. Moreover, when the multi-stage binarization processing is applied to the luminosity image, it is preferable that the reference section length of the luminosity is set large in a region with high luminosity, and the reference section length of the luminosity is set small in a region with low luminosity.

With the multi-stage binarization processing, the judgment of shape described above is repeated for every island over the entire area of the sample. Then, the images of each of the islands are replaced with the shape resulting from a binarization processing with the maximum or minimum threshold value when the island has been judged to have a circular shape or the like, and with the threshold value. The second noise-eliminated image from which a noise caused by fibroblasts was eliminated is obtained in this way.

Next, cancer cells are quantitated from the second noise-eliminated image.

The cancer cell amount can be evaluated by integrating an index of cell amount for each pixel. Preferably, the cancer cell amount is evaluated by an estimated volume value. This is because colonies of the cancer cells develop three-dimensionally in the collagen gel embedding cultivation, and thus taking their thicknesses into consideration results in more accurate evaluation. The estimated volume value is obtained by determining an absorbance from the luminosity of each pixel and integrating the absorbance over the entire area of the sample. This is because the absorbance correlates with the cell thickness in each region.

According to the Lambert-Beer law, the following equation holds for the intensity of the incident light to the sample $I_0$, and the intensity of the transmitted light $I$;

$$I/I_0 = \exp(-\alpha L)$$

where, $\alpha$ is an absorption coefficient of the stained cancer cells, and L is the distance of light passage through the cancer cells, i.e., a thickness of the cancer cells. An absorbance A by the cancer cells in each pixel is given by the following equation:

$$A = -\log(I/I_0)$$

$$= (\alpha L)/2.303$$

and therefore, the absorbance A is proportional to the thickness L of the cancer cells. The absorbance A is an index of cell amount in the pixel. The absorbance A is integrated over the entire area of the sample to determine the volume of cells. Note that log is common logarithm.

On the other hand, from the second noise-eliminated image, the absorbance A is determined by the following equation:

$$A = \log(S/T)$$

where, S is the number of gradations in the image, and T is the luminosity of the image.

Based on the above, the estimated volume value V of cancer cell amount is determined by the following equation:

$$V = \Sigma L = C \Sigma A = C \Sigma \{\log(S/T)\} \qquad \text{(Equation 1)}$$

where C is a constant. Thus, the absorbance is determined from the luminosity of each pixel, and the absorbance is integrated over the entire area of the sample to determine the estimated volume value of cells.

Note that, when the luminosity T is zero (when the luminosity of the original image was equal to the luminosity B of the dark image) with respect to a certain pixel for some reason, the denominator of the antilogarithm of the right-side logarithm in Equation 1 is 0, and calculation becomes impossible. As a measure, it is preferable that the intensity of the light source etc. are adjusted so that the image of the sample is not too dark, and a suitable exceptional processing is carried out.

As an easy method, the luminosity of each pixel may be integrated to determine the absorbance from the integrated value. The estimated volume value $V_p$ is represented by the following equation:

$$V_p = C_p A_p = C_p \log(nS/\Sigma T)$$

where, $C_p$ is a constant, $A_p$ is an absorbance, and n is a number of pixels (number of divided regions). In this equation, the absorbance is determined regarding the entire area of the sample as one region, but if the cell amount is large, in a case of using surgical material as a starting material, sufficient precision can be obtained. Also by using this equation, the influence of noise due to dusts and the like has already been eliminated by the image processing described above.

In the anticancer agent susceptibility test, the susceptibility to the anticancer agent is evaluated by comparing the cancer cell amounts after cultivation between the control sample to which the anticancer agent has not been added and the sample to which the anticancer agent has been added.

The effect of the cancer cell-quantitating method of this embodiment will be described again.

Noises due to dusts and bubbles have been difficult to eliminate by conventional techniques. According to the method of the present embodiment, the first light and the second light are used to eliminate the influences of contamination of dust and remaining bubbles, so that the cancer cell can be precisely quantitated. Since opaque dusts are misrecognized as cancer cells and furthermore misrecognized as thick cancer cells because of its dark shadow in the image if only the first image is used, quantitative precision is significantly impaired. Also, bubbles are misrecognized as cancer cells only with the first image, and many of the bubbles are larger than colonies of cancer cells, thus quantitative precision is significantly impaired.

Furthermore, by the multi-stage binarization processing, even if there is a portion in which cancer cells and fibroblasts are densely mixed, influence of the fibroblasts can be eliminated so that the cancer cells can be precisely quantitated.

Furthermore, the absorbance is determined and integrated for each of the divided regions in the image of the sample according to the above equation 1, so that the estimated volume value of cancer cells can be calculated more precisely.

Next, a second embodiment of the cell measurement method of the present invention will be described.

This embodiment relates to a method for quantitating cancer cells in an anticancer agent susceptibility test as in the first embodiment. In the method of this embodiment, the method for taking the first image and the second image is different from that in the first embodiment. The other steps are the same as in the first embodiment.

In this embodiment, the first light source emitting the first light and the second light source emitting the second light are sequentially lighted, and one camera takes an image each time each light source is lighted. Thereby, the first image is obtained by imaging at the time of lighting the first light source, and the second image is obtained by imaging at the time of lighting the second light source. The physical form of the light source is not particularly limited also in this embodiment. For example, an LED chip as a first light source and an LED chip as a second light source may be incorporated in one LED package, or otherwise separate LED packages as a first light source and a second light source may be used and alternately arranged.

In this embodiment, a monochrome camera can be used. In that case, finer images can be obtained, because monochrome cameras are available with higher resolution than color cameras.

Next, a third embodiment of the cell measurement method of the present invention will be described.

This embodiment relates to a method for quantitating cancer cells in an anticancer agent susceptibility test as in the first embodiment. The method of this embodiment is different from the first embodiment in that absorbance images are used as the first image and the second image, and elimination of noises due to dusts or the like and elimination of noises due to fibroblasts by a multi-stage binarization are applied to these absorbance images.

First, for each image obtained by color-separating an original image, an absorbance is determined from luminosity for each pixel, and it is quantized for example to 256 gradations so as to obtain a first image and a second image which are absorbance images. Respective pixels are compared between the first image and the second image. If the difference or the ratio of the absorbance is less than a predetermined threshold value, the region of the relevant pixel is judged to have no cancer cell and is excluded. When the difference in absorbance is defined as a reference for the threshold value, for example the threshold value can be set to one eighth of the gradation number of absorbance. Alternatively, in a case that the ratio of the absorbance is defined as a reference, when the ratio in absorbance between the first image and the second image is lower than a predetermined threshold value, relevant pixel may be excluded. More preferably, these threshold values are determined by a preliminary experiment. This processing is repeated for every pixel over the entire area of the sample, so that a first noise-eliminated image is obtained. The first noise-eliminated image is also an absorbance image.

Next, a multi-stage binarization processing is applied to the first noise-eliminated image. In this embodiment, since a binarization target is an absorbance image, the threshold value of the binarization is also a quantized absorbance. For the same reason as in the first embodiment, when the absorbance is quantized with 8 bits (0 to 255 grades), the reference section length of the absorbance is set to preferably 50 or less, more preferably 40 or less, and preferably 10 or more, more preferably 20 or more. Note that, if the quantization bit number is not 8 bits, a preferable section of the threshold value may be determined using the same proportion depending on the quantization bit number.

The multi-stage binarization processing is repeated for every island over the entire area of the sample, so that a second noise-eliminated image is obtained from which noises due to fibroblasts were eliminated. The second noise-eliminated image is also an absorbance image.

Next, cancer cells are quantitated from the second noise-eliminated image. Estimated volume values of cancer cells can be calculated by integrating the values of respective pixels of the second noise-eliminated image.

This embodiment is advantageous when the sample has a portion in which cancer cells are crowded. The luminosity of the image is not proportional to the thickness of the cancer cells. If the cancer cells overlap over a certain level of thickness, luminosity of a transmission image for a second light is decreased more than luminosity of a transmission image for a first light so that the difference in the luminosity between both images is reduced. Thus, there is a risk of excluding cancer cells, especially highly crowded cancer cells, in the step of eliminating noises due to dusts or the like. Whereas, since absorbance is proportional to the thickness of the cancer cells, there is no such problem as long as absorbance images are used.

EXAMPLE

Examples of the multi-stage binarization processing of the above-mentioned embodiments will be described.

A primarily cultured cancer cell obtained by applying a cell separation/dispersion treatment to gastric cancer tissues sampled from a living body was cultured by a collagen gel embedding method. As a collagen gel solution for embedding the cell, 1 volume of a ten-time concentrated Ham's F12 medium (containing no sodium bicarbonate) and 1 volume of a buffer solution for reconstitution (50 mM-NaOH solution containing 260 mM of sodium bicarbonate and 200 mM of HEPES) were added to 8 volumes of Cell Matrix Type CD (KURABO INDUSTRIES LTD.), and stored in ice. The cell was added to the collagen solution so that its final density was $2\times10^4$ cells/mL, and mixed well to prepare a collagen mixture. Ten µL of this collagen mixture was dropped into each of three wells of a 24-well plate with appropriate intervals using a micro pipette. Thereafter, the mixture was warmed in a $CO_2$ incubator at 37° C. for 1 hour to prepare a collagen matrix containing the cell. To the resulting collagen gel matrix, 1 mL of DF medium containing 10% FBS was added, and cultured for 160 hours. Then, an NR stain was injected into the wells, followed by formalin fixation and drying, to obtain a dried collagen gel.

The resulting dried collagen gel was placed on a sample stage and illuminated from below with an illumination, and a transmission image was imaged by a color camera. For the illumination, one LED package (MC-E Color, CREE Inc.) was used. RGB three-color LED chips were mounted in the LED package, and among them, only R chip and G chip were lighted for use. The first light was green light with a dominant wavelength of 528 nm, and the second light was red light with a dominant wavelength of 625 nm. For the color camera (XCL5005CR, Sony Corporation), the pixel number was 2448×2050, each of the RGB chips was constituted with 8-bit gradation, and a lens of 1.3 optical magnifications was used. At this time, the resolution of the image was about 2.7 µm.

The imaged original image was color-separated into three colors of RGB, and the G image was defined as a first image and the R image was defined as a second image. For each pixel, the first image and the second image were compared, and when a difference in luminosity was 36 or more, the pixel was judged to be a first noise and eliminated from the image. For the remaining pixels, the absorbance was calculated from the pixel value of the G image, and an absorbance image having a pixel value obtained by quantizing the resulting absorbance with 8 bits was made. A multi-stage binarization processing was applied to this image in which a reference section length (=reference difference) was set to 30, and when each island in the image was round or a percentage of arcs with respect to a contour of the island was 60% (reference percentage) or more, it was judged that the island was composed of cancer cells.

The multi-stage binarization processing was specifically performed while varying the threshold value like 30, 50, 60, 40, 60, 70, 50, 70, 80, . . . , and when the island-like section was substantially circular in two multi-stage binarization processings using two threshold values having a difference of 30 or more, it was judged that the island was composed of cancer cells. Note that the threshold value was irregularly varied just to facilitate analysis of effect of this embodiment, and it was essentially unnecessary. It is preferable to perform the binarization processing while sequentially increasing or decreasing the threshold value to suppress wasteful processings. In this embodiment, since the reference section length is set to 30, the same result as above can be obtained as a matter of course if the multi-stage processings are performed while sequentially increasing or decreasing the threshold values by 10 every time and it is judged that the island is composed of cancer cells when the island has a circular shape or the like in each of the three processings.

FIG. 12A shows the original image, and FIG. 12B shows the image obtained by eliminating the first noise from this original image and binarizing the absorbance image with the threshold value of 3. In the lower left of FIGS. 12A and 12B, there is a portion in which cancer cells and fibroblasts are densely mixed.

Figure 13:
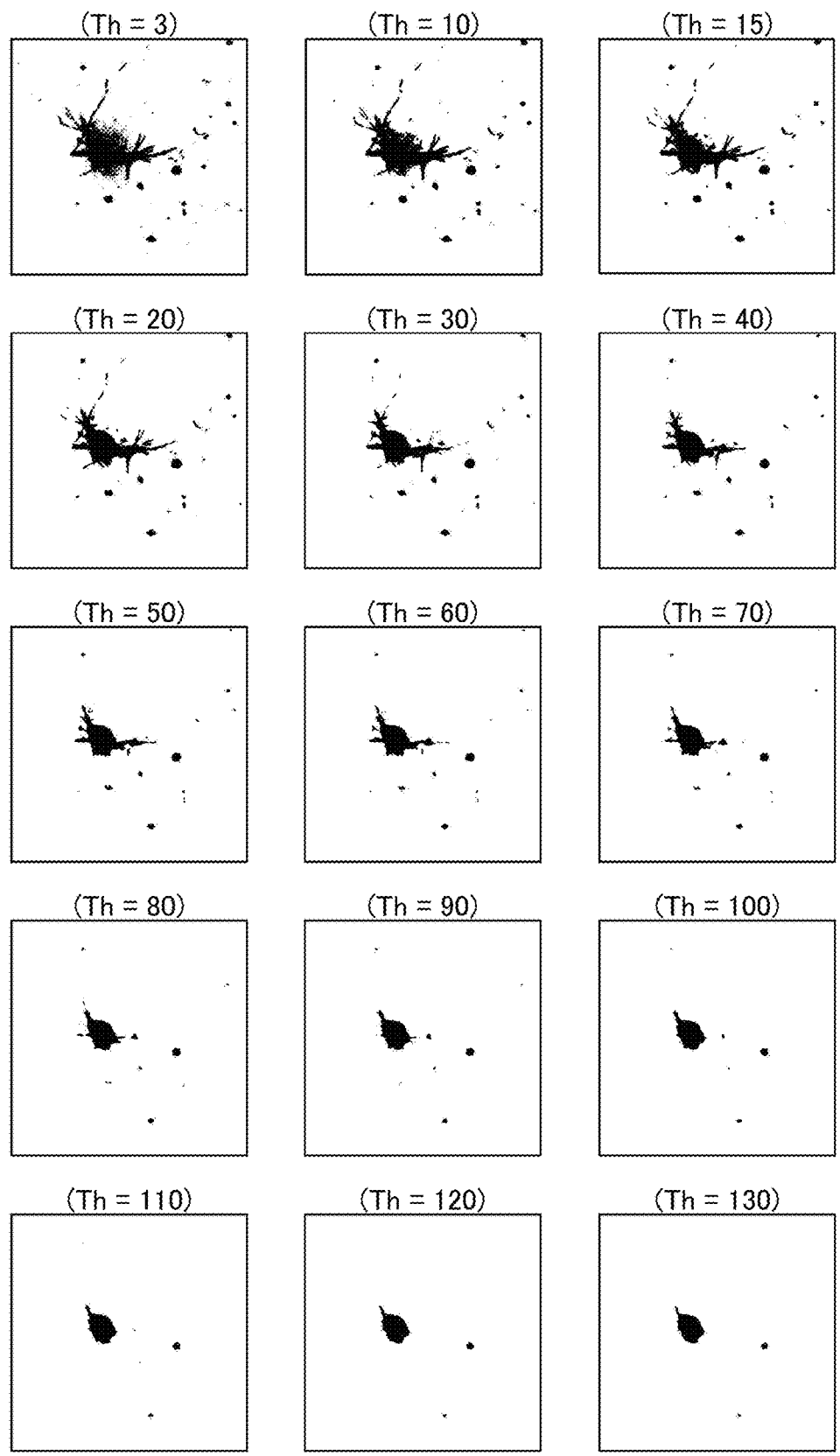
FIG. 13 shows results of the binarization processings to different threshold values in Example.
Figure 14:
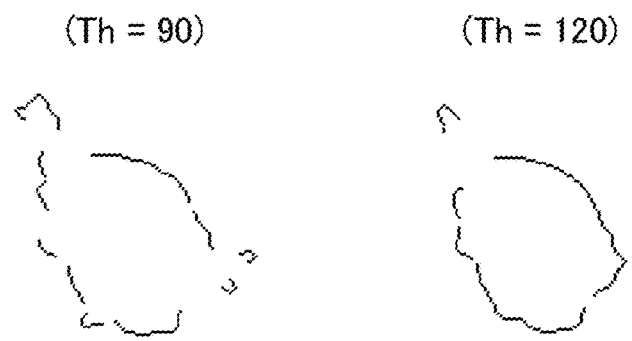
FIG. 14 shows arcs in a contour of the island-like section in Example.

FIG. 13 shows images of cases where the binarization processings with different threshold values are applied to an area surrounded by a square in the lower left of FIGS. 12A and 12B. "Th" in the figure is a value of the threshold value. This island is not round in all of the binarized images having the threshold value of 3 to 130. However, the percentage of arcs with respect to the contour of the island was 60% or more in each of the binarized images having the threshold value of 90, 100, 110, 120, 130. Since the percentage of arcs with respect to the contour of the island was greater than or equal to the reference percentage when the threshold value was 90 and 120, this island was judged to be an aggregate of cancer cells. For reference, FIG. 14 shows arcs with respect to the contour of the island when the threshold value is 90 and 120.

Now, an Experimental Example to obtain the first noise-eliminated image will be described.

A human colon cancer-derived cell line HCT-116 was used as a cancer cell, and cultured by a collagen gel embedding method. As a collagen gel solution for embedding the cell, 1 volume of a ten-time concentrated Ham's F12 medium (containing no sodium bicarbonate) and 1 volume of a buffer solution for reconstitution (50 mM-NaOH solution containing 260 mM of sodium bicarbonate and 200 mM of HEPES) were added to 8 volumes of Cell Matrix Type CD (KURABO INDUSTRIES LTD.), and stored in ice. The HCT-116 strain was added to the collagen solution so that its final density was $4\times10^4$ cells/mL, and mixed well to prepare a collagen mixture. 10 µL of this collagen mixture was dropped into each of three wells of a 24-well plate with appropriate intervals using a micro pipette. Thereafter, the mixture was warmed in a $CO_2$ incubator at 37° C. for 1 hour to prepare a collagen matrix containing the cancer cell. To the resulting collagen gel matrix, 1 mL of DF medium containing 10% FBS was added, and cultured for 16 hours. Then, an NR stain was injected into the wells, followed by formalin fixation and drying, to obtain a dried collagen gel.

The resulting dried collagen gel was placed on a sample stage and illuminated from below with an illumination, and a transmission image was imaged by a color camera. For the illumination, one LED package (MC-E Color, CREE Inc.) was used. RGB three-color LED chips were mounted in the LED package, and among them, only R chip and G chip were lighted for use. The first light was green light with a dominant wavelength of 528 nm, and the second light was red light with a dominant wavelength of 625 nm. For the color camera (XCL5005CR, Sony Corporation), the pixel number was 2448×2050, each of the RGB chips was constituted with 8-bit gradation, and a lens of 1.3 optical magnifications was used. At this time, the resolution of the image was about 2.7 µm.

Figure 6:
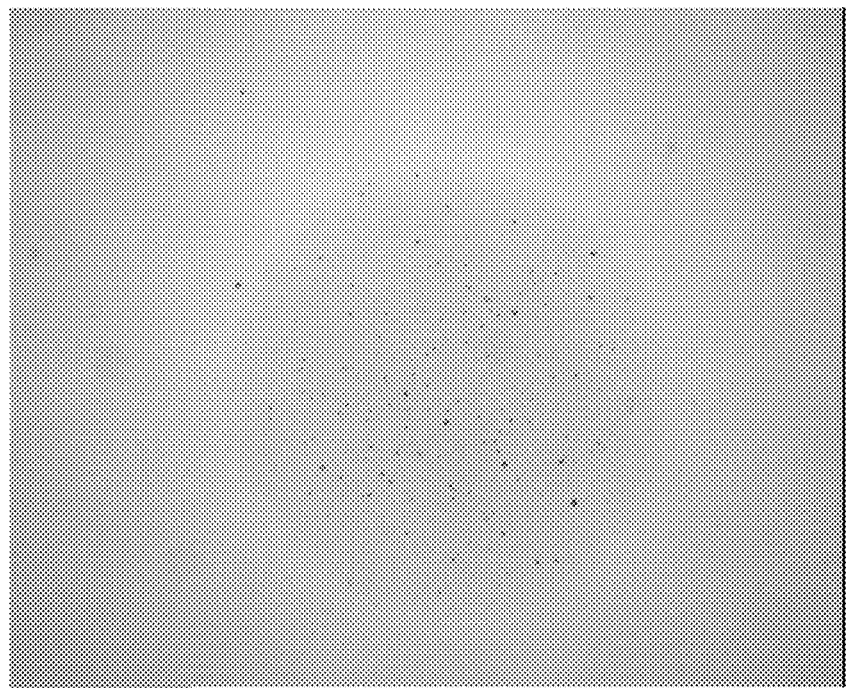
FIG. 6 is an original image of a sample in which cancer cells were quantitated in Experimental Example.
Figure 7:
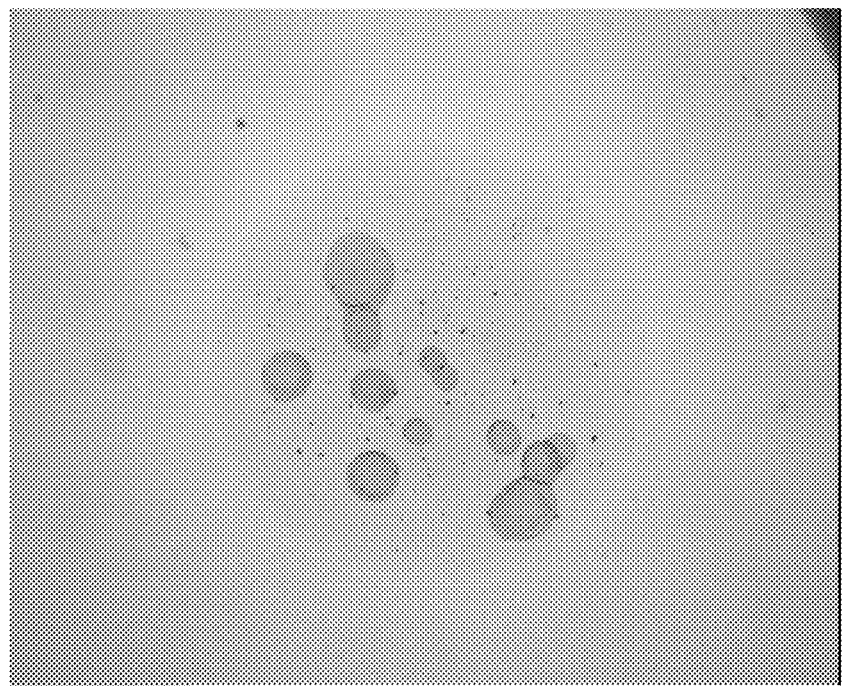
FIG. 7 is an original image of a sample in which cancer cells were quantitated in Experimental Example.
Figure 8:
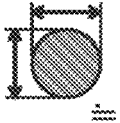
FIG. 8 is a diagram for explaining a method of judging whether or not an island-like section on the image is substantially circular.

In FIG. 6 (sample containing no bubble) and FIG. 7 (sample containing many bubbles), the imaged original images were converted into monochrome images. The samples shown in FIGS. 6 and 7 contain almost the same amount of cancer cell. Note that the above FIG. 4 also shows an image obtained by the same method as this Experimental Example. The original image was color-separated into three colors of RGB, and the G image was defined as a first image and the R image was defined as a second image. For each pixel, the first image and the second image were compared, and when a difference in luminosity was within 35, the pixel was judged to have no cancer cell. Absorbance was calculated for each pixel according to the above Equation 1, and integrated over the entire area of the sample to determine an estimated volume value of the cancer cell. At this time, a value of the constant C in Expression 1 was $2.0\times10^{-4}$.

As Comparable Experimental Example, the absorbance was calculated from the luminosity of the first image without using the second image, and similarly integrated over the entire area of the sample to determine an estimated volume value of the cancer cell.

The estimated volume values obtained by the method of Experimental Example were 0.42 in FIG. 6 and 0.44 in FIG. 7. In the method of Comparable Experimental Example, the estimated volume values were 0.47 in FIG. 6 and 1.54 in FIG. 7. In FIG. 6 without bubbles, Experimental Example and Comparable Experimental Example showed equivalent estimated volume values. On the other hand, in FIG. 7 with many bubbles, the estimated volume value according to Comparable Experimental Example was about three times that of Experimental Example. This was attributed to the influence of the noise due to the bubbles. In Comparable Experimental Example the noise due to the bubbles could be eliminated.

The cell measurement method of the present invention is not limited to the above-described Embodiments and Example, and can be variously modified within the scope of the technical idea of the invention.

For example, in the above-described Embodiment, relativization of the luminosity (blank correction), elimination of noises such as dusts and bubbles by comparison between the first image and the second image, and elimination of noises due to fibroblasts are carried out in this order, but their turns may be replaced.

For example, images may be taken using a white illumination while sequentially switching color filters installed in front of the camera, to obtain the first and second images.

For example, images may be taken by a color camera using a white light source having continuous spectrum as an illumination, and color-separated to obtain the first and second images. However, since image sensor elements of the color camera generally have wide sensitivity spectra and partially overlap with each other, it had better use two light sources having different wavelengths for obtaining clear difference between the first and second images.

What is claimed is:

1. A cell measurement method comprising:
   a step of staining target cells with a dye;
   an image obtaining step for obtaining an image of the target cells;
   a discrimination step for discriminating the target cells from contaminating cells by applying multi-stage binarization processing to the image;
   a step of eliminating noises due to the contaminating cells from the image based on the result of the discrimination step; and
   a step of evaluating an amount of target cells by integrating an index value of cell amount in the image from which the contaminating cells have been eliminated,
   wherein when an island-like section is substantially circular in two binarization processings by using two threshold values which are different by a predetermined reference difference or more, and thus it can be estimated that the island-like section is substantially circular between these two threshold values regardless of the magnitude of the threshold values, the discrimination step comprises a step of judging that the island-like section is substantially spherical cells.

2. A cell measurement method comprising:
   a step of staining target cells with a dye;
   an image obtaining step for obtaining an image of the target cells;
   a discrimination step for discriminating the target cells from contaminating cells by applying multi-stage binarization processing to the image;
   a step of eliminating noises due to the contaminating cells from the image based on the result of the discrimination step; and
   a stet of evaluator an amount of target cells by integrating an index value of cell amount in the image from which the contaminating cells have been eliminated,
   wherein when a percentage of arcs with respect to a contour of an island-like section is greater than or equal to a predetermined value in two binarization processings by using two threshold values which are different by a predetermined reference difference or more, and thus it can be estimated that the percentage of the arcs with respect to the contour of the island-like section is greater than or equal to the predetermined value between the two threshold values regardless of the magnitude of the threshold values, the discrimination step comprises a step of judging that the island-like section is an aggregate of substantially spherical cells.

3. The cell measurement method according to claim 1, wherein in the discrimination step, the binarization processings are performed while sequentially increasing or decreasing the threshold values.

4. The cell measurement method according to claim 1, wherein the target cells are cancer cells and the contaminating cells are fibroblasts.

5. The cell measurement method according to claim 1, wherein the target cells are cells cultured by being embedded in a collagen gel.

6. The cell measurement method according to claim 1, wherein the image is a luminosity image of a transmission image obtained by imaging the target cells.

7. The cell measurement method according to claim 1, wherein the image is an absorbance image based on a transmission image obtained by imaging the target cells.

8. The cell measurement method according to claim 1, wherein the index value of cell amount is an absorbance, and the evaluating the amount of target cells is performed by calculating an estimated volume value of the target cells.

9. The cell measurement method according to claim 1, wherein the image obtaining step consists of:
   a step of obtaining a first image and a second image which are transmission images for a first light and a second light to which the dye has different absorbance; and
   a step of obtaining a first noise-eliminated image by dividing each of the first image and the second image into a plurality of divided regions and comparing the first image and the second image for each of the divided regions so as to eliminate noises.

10. The cell measurement method according to claim 9, wherein the first image and the second image are obtained on the basis of the transmission image taken with one color camera while concurrently applying the first light and the second light.

11. The cell measurement method according to claim 9, wherein the first image and the second image are obtained on the basis of the transmission image obtained by independently taking each image using one camera while sequentially applying the first light and the second light.

12. The cell measurement method according to claim 2, wherein in the discrimination step, the binarization processings are performed while sequentially increasing or decreasing the threshold values.

13. The cell measurement method according to claim 2, wherein the target cells are cancer cells and the contaminating cells are fibroblasts.

14. The cell measurement method according to claim 2, wherein the target cells are cells cultured by being embedded in a collagen gel.

15. The cell measurement method according to claim 2, wherein the image is a luminosity image of a transmission image obtained by imaging the target cells.

16. The cell measurement method according to claim 2, wherein the image is an absorbance image based on a transmission image obtained by imaging the target cells.

17. The cell measurement method according to claim 2, wherein the index value of cell amount is an absorbance, and the evaluating the amount of target cells is performed by calculating an estimated volume value of the target cells.

18. The cell measurement method according to claim 2, wherein the image obtaining step consists of:
   a step of obtaining a first image and a second image which are transmission images for a first light and a second light to which the dye has different absorbance; and
   a step of obtaining a first noise-eliminated image by dividing each of the first image and the second image into a plurality of divided regions and comparing the first image and the second image for each of the divided regions so as to eliminate noises.

19. The cell measurement method according to claim 18, wherein the first image and the second image are obtained on the basis of the transmission image taken with one color camera while concurrently applying the first light and the second light.

20. The cell measurement method according to claim 18, wherein the first image and the second image are obtained on the basis of the transmission image obtained by independently taking each image using one camera while sequentially applying the first light and the second light.

* * * * *